(12) United States Patent
LaPosta et al.

(10) Patent No.: US 6,635,261 B2
(45) Date of Patent: Oct. 21, 2003

(54) ADJUVANT AND VACCINE COMPOSITIONS CONTAINING MONOPHOSPHORYL LIPID A

(75) Inventors: Vincent James LaPosta, Pittsford, NY (US); John Hayward Eldridge, Fairport, NY (US)

(73) Assignee: Wyeth Holdings Corporation, Madison, NJ (US)

(*) Notice: Subject to any disclaimer, the term of this patent is extended or adjusted under 35 U.S.C. 154(b) by 202 days.

(21) Appl. No.: 09/943,028

(22) Filed: Aug. 30, 2001

(65) Prior Publication Data

US 2002/0025330 A1 Feb. 28, 2002

Related U.S. Application Data

(62) Division of application No. 09/352,526, filed on Jul. 13, 1999, now Pat. No. 6,306,404.

(51) Int. Cl.$^7$ .......................... A61K 47/00; A61K 45/00; A61K 39/00; A61K 39/12; A61K 39/02
(52) U.S. Cl. ...................... 424/278.1; 424/283.1; 424/184.1; 424/204.1; 424/234.1; 424/275.1; 424/277.1
(58) Field of Search .................... 424/278.1, 283.1, 424/184.1, 204.1, 234.1, 275.1, 277.1

(56) References Cited

U.S. PATENT DOCUMENTS

| | | | |
|---|---|---|---|
| 4,206,200 A | 6/1980 | Guthohrlein | 424/92 |
| 4,673,574 A | 6/1987 | Anderson | 424/92 |
| 4,710,378 A | 12/1987 | Outomo et al. | 424/89 |
| 4,761,283 A | 8/1988 | Anderson | 424/92 |
| 4,902,506 A | 2/1990 | Anderson et al. | 424/88 |
| 4,912,094 A | 3/1990 | Myers et al. | 514/54 |
| 5,097,020 A | 3/1992 | Anderson et al. | 530/403 |
| 5,151,265 A | 9/1992 | Hwang-Felgner et al. | 424/85.5 |
| 5,360,897 A | 11/1994 | Anderson et al. | 530/403 |
| 5,372,928 A * | 12/1994 | Miyamura et al. | 435/5 |
| 5,750,110 A | 5/1998 | Prieels et al. | 424/208.1 |
| 5,750,332 A * | 5/1998 | Robey et al. | 435/5 |
| 5,776,468 A | 7/1998 | Hauser et al. | 424/226.1 |
| 5,824,538 A * | 10/1998 | Branstrom et al. | 435/252.1 |
| 5,965,714 A * | 10/1999 | Ryall | 530/402 |

FOREIGN PATENT DOCUMENTS

| | | |
|---|---|---|
| EP | 0812593 | 12/1997 |
| EP | 0909562 | 1/1998 |
| GB | 2220211 A | 4/1990 |
| WO | 9206113 | 4/1992 |
| WO | 9300807 | 1/1993 |
| WO | 9319780 | 10/1993 |
| WO | 9419013 | 1/1994 |
| WO | 9406468 | 3/1994 |
| WO | 9400153 | 6/1994 |
| WO | 9421292 | 9/1994 |
| WO | 9517209 | 6/1995 |
| WO | 9517210 | 6/1995 |
| WO | 9626741 | 9/1996 |
| WO | 9631236 | 10/1996 |
| WO | 9801139 | 1/1998 |

OTHER PUBLICATIONS

Vaccine Design, The Subunit and Adjuvant Approach, Pharmaceutical Biotecchnology, vol. 6, Edited by M.F. Powell and M. J. Newman, pp. 495–524, Chapter 21, (1995).
Wolfgang K. Joklik et al., Editor, Zinsser Microbiology 20th Edition, Contents, pp. iii–v(1992).
John C. Sherrisetal Editor, Medical Microbiology, Second Edition. Contents, pp. vii–xi (1990).
Gennaro, Alfonso R., Remington's 18th Edition, 1565–1567 (1990).
International Search Report PCT/US99/15942.

* cited by examiner

*Primary Examiner*—James Housel
*Assistant Examiner*—Shanon Foley
(74) *Attorney, Agent, or Firm*—Daniel B. Moran; Thomas S. Szatkowski

(57) ABSTRACT

The invention pertains to adjuvant and vaccine compositions of monophosphoryl lipid A, sugar and optionally an amine based surfactant, which when frozen and thawed or lyophilized and reconstituted reform a colloidal suspension having a light transmission of greater than or equal to 88% as measured spectrophotometrically.

18 Claims, No Drawings

ADJUVANT AND VACCINE COMPOSITIONS CONTAINING MONOPHOSPHORYL LIPID A

CROSS REFERENCE TO RELATED APPLICATIONS

This is a divisional of application Ser. No. 09/352,526 filed on Jul. 13, 1999 now U.S. Pat. No. 6,306,404, the entire disclosure of which is herein incorporated by reference, which application claims the benefit of U.S. patent application Ser. No. 09/115,392 filed Jul. 14, 1998, which was converted to a Provisional Application herein incorporated by reference pursuant to a petition filed under 37 C.F.R. 1.53 (c) (2) filed Nov. 4, 1998.

BACKGROUND OF THE INVENTION

1. Field of the Invention

This invention relates to improved adjuvant and vaccine compositions, methods for preparing said improved adjuvant and vaccine compositions, and methods of using the improved compositions.

2. Description of the Prior Art

Conventional vaccines have been used for many years to protect humans and animals from a wide variety of infectious diseases. Typically, these conventional vaccines contain one or more antigens which may include an attenuated pathogen, killed pathogen, or an immunogenic component of a pathogen. In some vaccines, the antigen or antigens may be employed alone to elicit protective immune responses. In other vaccines, the antigen or antigens may be employed together with one or more adjuvants to enhance the immunogenicity of an antigen. One such adjuvant known to the art is monophosphoryl lipid A, which is derived from the lipopolysaccharide of *Salmonella minnesota* R595. It is also known to the art that monophosphoryl lipid A is a lipidic material which spontaneously aggregates with itself in an aqueous environment. Moreover, it is known that the degree of aggregation has an effect on the activity of monophosphoryl lipid A as an immunostimulant in that the aggregated monophosphoryl lipid A is less stimulatory.

Monophosphoryl lipid A is typically obtained as the triethylamine salt in the form of a lyophilized white powder. Being very hydrophobic, the lyophilized monophosphoryl lipid A does not readily form a clear solution when reconstituted with water but instead yields a turbid mixture with visible white particulates of heterogeneous size that settle out and further aggregate upon standing. To make an acceptable aqueous preparation of monophosphoryl lipid A, it is known to suspend the lyophilized monophosphoryl lipid A triethylamine salt at 1 to 2 mg/mL (w/v) in water containing 0.2% triethylamine, to heat the suspension at 65–70° C., and then to sonicate the mixture. The resulting aqueous preparation, slightly opalescent or clear, is an aqueous colloidal suspension. The triethylamine aids in the solubilization of the monophosphoryl lipid A and may be substituted with similar amounts of triethanolamine.

When aqueous preparations of monophosphoryl lipid A prepared as described hereinabove are frozen and then thawed, however, the monophosphoryl lipid A aggregates resulting in a turbid mixture quite similar in appearance to the turbid mixture of monophosphoryl lipid A prior to sonication. Similarly, when an aqueous preparation of monophosphoryl lipid A as described hereinabove is lyophilized and then rehydrated, the result is also a turbid mixture of aggregated monophosphoryl lipid A.

SUMMARY OF THE INVENTION

The present invention provides to the art a lyophilized composition containing monophosphoryl lipid A, which composition exhibits an enhanced reconstitution feature and which avoids the settling out and aggregation problems of the prior art. In particular, the present invention provides a lyophilized composition comprising monophosphoryl lipid A, sugar and, optionally, an added amine based surfactant, and is capable of being reconstituted or rehydrated with an aqueous diluent to form, without further sonication, an aqueous colloidal suspension of monophosphoryl lipid A having a light transmission of at least 88%, as measured spectrophotometrically. The lyophilized composition according to the present invention comprises up to about 5 wt % monophosphoryl lipid A, greater than about 70 wt % sugar and from about 0 to about 30 wt % optionally added amine based surfactant, said wt % based on the total of the weights of monophosphoryl lipid A, sugar and, if present, amine based surfactant. Preferably, the lyophilized composition according to the present invention comprises up to about 5 wt % monophosphoryl lipid A, from about 70 to about 99.99 wt % sugar and from about 0 to about 28 wt % optionally added amine based surfactant. More preferably, the lyophilized composition according to the present invention comprises up to about 4 wt % monophosphoryl lipid A, from about 75 to about 99.99 wt % sugar and from about 0 to about 22 wt % optionally added amine based surfactant. The lyophilized composition may further comprise an immunologically effective amount of an antigen or antigens. The lyophilized composition of the present invention may be reconstituted or rehydrated with an aqueous diluent at concentrations up to about 210 mg of lyophilized composition per ml of aqueous diluent, preferably from about 10 mg of lyophilized composition per ml of aqueous diluent to about 210 mg of lyophilized composition per ml of aqueous diluent, to form, without further sonication, an aqueous colloidal suspension.

Another aspect of the present invention is a method of preparing an aqueous colloidal suspension of monophosphoryl lipid A in which the aqueous colloidal suspension is frozen for storage and then thawed for use without the problems of settling out and aggregation known in the prior art. By this method, monophosphoryl lipid A is mixed in an aqueous diluent and optionally with an amine based surfactant and also optionally an antigen or antigens. An aqueous colloidal suspension is formed by sonicating, optionally with heating, or other known methods, as described in greater detail hereinafter. Sugar, in an amount from about 10 mg/ml to about 200 mg/ml, is added to the mixture either before or after the formation of an aqueous colloidal suspension. The sugar may be in the form of a solid or in the form of an aqueous solution. The resulting aqueous colloidal suspension may then be frozen. Thawing the frozen aqueous colloidal suspension affords without further sonication an aqueous colloidal suspension containing monophosphoryl lipid A having a light transmission of greater than or equal to 88%, as measured spectrophotometrically. An antigen or antigens, as defined hereinafter, may be added to the thawed aqueous colloidal suspension to form a vaccine composition which may be administered to a vertebrate. Alternatively, if the aqueous colloidal suspension contains an antigen before freezing, the vaccine composition may be thawed and administered to a vertebrate.

The aqueous colloidal suspensions of the present invention are a special type of liquid suspension in which the particles of suspended monophosphoryl lipid A are present in very finely divided but not in dissolved form. The aqueous colloidal suspensions containing monophosporyl lipid A, sugar and, optionally, an amine based surfactant according to the present invention are true suspensions not solutions, and do not have the property, unlike ordinary suspensions of monophosphoryl lipid A, of settling out and aggregation. The presence of the aqueous colloidal suspensions of the present invention can be determined by light transmission. Thus, an aqueous colloidal suspension containing monophosphoryl lipid A, sugar and optionally an amine based surfactant according to the present invention is one which exhibits a light transmission of greater than or equal to 88%, as measured spectrophotometrically.

The present invention solves the settling out and aggregation problems of the prior art, by providing the addition of sugar to an aqueous colloidal suspension of monophosphoryl lipid A prior to freezing or lyophilization. The sugar may be added either before or after formation of the aqueous colloidal suspension but must be added before freezing or lyophilization of the suspension. The addition of sugar to an aqueous colloidal suspension of monophosphoryl lipid A prior to freezing or lyophilization provides a composition which, after freezing can be thawed to afford an aqueous colloidal suspension without further sonication or, alternatively, after lyophilization, can be reconstituted with a suitable aqueous diluent and afford without further sonication an aqueous colloidal suspension as described hereinabove. Suitable sugars include the monosaccharides, dextrose, mannose, galactose and fructose as well as the disaccharides sucrose, lactose, isomaltose, maltose and trehalose. Mixtures of sugars, for example sucrose and dextrose, may also be employed. These sugars are all non toxic and pharmaceutically acceptable. Preferred are sucrose and dextrose. The sugar may be in the form of a solid or in the form of an aqueous solution. Suitable aqueous diluents include water or saline and can also include an antigen or antigens and, may additionally contain preservatives or additional adjuvants, or other pharmaceutically acceptable additives, vehicles, or carriers. Suitable amine based surfactants include triethylamine (TEA) and triethanolamine (TEM).

A further aspect of the invention is a reconstituted or rehydrated aqueous colloidal suspension which, despite the elimination of a further sonication step, is obtained upon reconstitution of the lyophilized composition described hereinabove with an aqueous diluent. As discussed hereinabove, before the present invention, a sonication step was necessary in order to obtain an aqueous colloidal suspension containing monophosphoryl lipid A. However, it has now been found that when an aqueous diluent is added to the lyophilized composition described hereinabove, an aqueous colloidal suspension containing monophosphoryl lipid A is obtained without further sonication. The reconstituted aqueous colloidal suspension so obtained exhibits a light transmission of greater than or equal to 88%, when measured spectrophotometrically. Surprisingly, the reconstituted aqueous colloidal suspension so obtained is capable of being frozen and, after thawing, again reforming an aqueous colloidal suspension which exhibits a light transmission of greater than or equal to 88%. The reconstituted aqueous colloidal suspension of the present invention comprises up to about 2.5 mg of monophosphoryl lipid A per ml of aqueous diluent, from about 10 to 200 mg of sugar per ml of aqueous diluent, and from about 0 to about 6 mg of amine based surfactant per ml of aqueous diluent. Preferably, the reconstituted aqueous colloidal suspension of the present invention comprises up to about 2.0 mg of monophosphoryl lipid A per ml of aqueous diluent, from about 20 to 150 mg of sugar per ml of aqueous diluent and from about 0 to about 3 mg of amine based surfactant per ml of diluent. The reconstituted aqueous colloidal suspension may further comprise an immunologically effective amount of an antigen or antigens. Suitable sugars, amine based surfactants and aqueous diluents are as described hereinabove.

A further aspect of the invention is a vaccine composition comprising the lyophilized composition and the reconstituted aqueous colloidal suspension described hereinabove in combination with an immunologically effective amount of an antigen or antigens. The effective amount of an antigen or antigens may be optionally provided in the aqueous diluent. In particular, the vaccine composition further comprises an immunologically effective amount of an antigen or antigens derived from or produced by a bacterium, a virus, a parasite, a cancer cell or an allergen. An effective amount of antigen is defined as that amount of antigen that when administered to an animal or a human evokes an immune response as measured by production of specific antibodies or cell-mediated effector mechanisms. Immunologically effective amounts of an antigen or antigens are in general from about 1 $\mu$g or less to 5 mg. An effective amount of the monophosphoryl lipid A adjuvant is the amount of monophosphoryl lipid A that when added to a vaccine will enhance the magnitude or quality or duration of the immune response to the antigen or antigens in the vaccine. An effective amount of the adjuvant monophosphoryl lipid A is in the range of about 1 $\mu$g to about 1 mg.

Suitable antigens for the vaccine compositions of the present invention include any entity capable of producing an antibody or cell-mediated immunological response directed specifically against that entity in a vertebrate exposed to the antigen. One or more antigens may be employed. The antigen or antigens may be derived from pathogenic microorganisms including viruses, bacteria, mycoplasmas, fungi, protozoa and other parasites. Further, the antigen or antigens may be derived from sources other than microorganisms, for example, cancer cells or allergens. The antigen or antigens may be all or part of a pathogenic microorganism, or all or part of a protein, glycoprotein, glycolipid, polysaccharide or lipopoly-saccharide which is associated with the organism, or the antigen or antigens may be a polypeptide or other entity which mimics all or part of such a protein, glycoprotein, glycolipid, polysaccharide or lipopolysaccharide.

Pathogenic microorganisms from which antigens may be produced or derived for vaccine purposes are well known in the field of infectious diseases, as listed in, for example, Medical Microbiology, Second Edition, (1990) J. C. Sherris (ed.), Elsevier Science Publishing Co., Inc., New York, and Zinsser Microbiology, 20th Edition (1992), W. K. Joklik et al. (eds.), Appleton & Lange Publishing Division of Prentice Hall, Englewood Cliffs, N.J. Examples of organisms of interest for human vaccines include Chlamydia, Nontypeable *Haemophilus influenzae, Helicobacter pylori, Moraxella catarrhalis, Neisseria gonorrhoeae, Neisseria meningitidis, Salmonella typhi, Streptococcus pneumoniae,* Group A Streptococcus, Group B Streptococcus, Herpes Simplex Virus, Human Immunodeficiency Virus, Human Papilloma Virus, Influenza, Measles, Parainfluenza, Respiratory Syncytial Virus, Rotavirus, Norwalk Virus, and others.

The antigen or antigens may include glycoconjugates which comprise polysaccharide antigen or antigens, for example, bacterial capsular polysaccharide or fragment thereof, chemically linked to a protein carrier molecule in order to enhance immunogenicity. Methods for preparing conjugates of bacterial capsular polysaccharide and protein carrier molecules are well known in the art and can be found, for example, in Dick and Burret, *Contrib Microbiol Immu-* nol. 10:48–114(Cruse J M, Lewis R E Jr., eds; Basel Kruger (1989). Suitable conjugates, including pneumococcal glycoconjugate, are described in greater detail in U.S. Pat. Nos. 4,673,574, 4,761,283, 4,902,506, 5,097,020 and 5,360,897 the contents of which are incorporated herein by reference.

Also provided is a method of immunizing a vertebrate through vaccination which comprises administrating an effective amount of a vaccine composition according to the present invention to said vertebrate.

Also provided is a method for the preparation of a lyophilized composition comprising:
 a. suspending monophosphoryl lipid A in an amount up to about 5 mg/ml and, optionally, an amine based surfactant in an amount from 0 to about 6 mg/ml in an aqueous diluent;
 b. forming an aqueous colloidal suspension having a light transmission of greater than or equal to 88%, as measured spectrophotometrically;
 c. adding sugar at about 10 to 200 mg/ml either before or after forming the aqueous colloidal suspension;
 d. lyophilizing the sugar containing aqueous colloidal suspension; and
 e. recovering a lyophilized composition.

Also provided is a method for preparing a lyophillized composition comprising:
 a. heating lipopolysaccharide of gram negative bacteria Salmonella minnesota R595 in a mineral acid of moderate strength for a sufficient period of time to obtain a monophosphoryl derivative;
 b. dissolving the monophosphoryl derivative in an organic solvent and drying;
 c. treating the monophosphoryl derivative with mild alkali to remove a base labile fatty acid chain at the position to yield 3-deacylated monophosphoryl lipid A;
 d. purifying the 3-deacylated monophosphoryl lipid A by liquid chromatography and recovering monophosphoryl lipid A;
 e. suspending monophosphoryl lipid A in an amount up to about 5 mg/ml and, optionally, an amine based surfactant in an amount from 0 to about 6 mg/ml in an aqueous diluent;
 f. forming an aqueous colloidal suspension having a light transmission of greater than or equal to 88%, as measured spectrophotometrically;
 g. adding sugar at about 10 to 200 mg/ml either before or after forming the aqueous colloidal suspension;
 h. lyophilizing the sugar containing aqueous colloidal suspension; and
 i. recovering a lyophilized composition.

Also provided is a method for the preparation of an aqueous colloidal suspension containing monophosphoryl lipid A capable of being frozen and thawed comprising:
 a. suspending monophosphoryl lipid A in an amount up to about 5 mg/ml and, optionally, an amine based surfactant in an amount from 0 to about 6 mg/ml in an aqueous diluent;
 b. forming an aqueous colloidal suspension having a light transmission of greater than or equal to 88%, as measured spectrophotometrically;
 c. adding sugar at about 10 to 200 mg/ml either before or after forming the aqueous colloidal suspension;
 d. freezing the sugar containing aqueous colloidal suspension; and
 e. thawing and recovering the aqueous colloidal suspension.

DESCRIPTION OF THE PREFERRED EMBODIMENTS

The preparation of monophosphoryl lipid A is described in U.S. Pat. No. 4,912,094, the contents of which are incorporated herein by reference. Briefly, monophosphoryl lipid A is produced by refluxing lipopolysaccharide (or lipid A) obtained from heptoseless mutants of gram negative bacteria, Salmonella minnesota R595, in mineral acid solutions of moderate strength (e.g., 0.1N HCl) for a period of approximately 30 minutes. Suitable mineral acids include hydrochloric, sulfuric and the like. This treatment results in the loss of the phosphate moiety at position 1 of the reducing-end glucosamine. The core carbohydrate is removed from the 6' position of the non-reducing glucosamine during this treatment. The result is a monophosphoryl derivative of lipid A. The monophosphoryl derivative of lipid A is dissolved in organic solvents and treated with very mild alkali which removes the base-labile fatty acid chain at the 3 position to yield 3-O-desacyl-4'-monophosphoryl lipid A, indicating that position 3 of the reducing end glucosamine is de-O-acylated. Chemically it is a mixture of 3-deacylated monophosphoryl lipid A with 4, 5 or 6 acylated chains. Suitable organic solvents include methanol (alcohols), dimethyl sulfoxide, dimethylformamide, chloroform, dichloromethane and the like as well as mixtures thereof. Combinations of water and one or more of these organic solvents also can be employed. Suitable alkaline bases can be chosen from among various hydroxides, carbonates, phosphates and amines. Illustrative bases include the inorganic bases such as sodium hydroxide, potassium hydroxide, sodium carbonate, potassium carbonate, sodium bicarbonate, potassium bicarbonate, and the like, and organic bases such as alkyl amines and include, but are not limited to, diethylamine, triethylamine and the like. The 3-O-desacyl-4'-monophosphoryl lipid A is purified by liquid chromatography and converted to the monobasic triethylamine (triethylammonium) salt.

The term monophosphoryl lipid A as used herein means 3-O-desacyl-4'-monophosphoryl lipid A as the monobasic triethylamine (triethylammonium)salt.

To prepare the lyophilized composition of the present invention, the monophosphoryl lipid A is added to an aqueous diluent, preferably water, in amounts up to 5 mg of monophosphoryl lipid A per ml of aqueous diluent, preferably up to 2.5 mg/ml and more preferably from about 0.5 to 2.5 mg/ml. Optionally, an added amine based surfactetnt in an amount from about 0 to about 6 mg/ml, preferably 0 to 3 mg/ml is employed.

An aqueous colloidal suspension having a light transmission of greater than or equal to 88%, as measured spectrophotometrically is formed by sonication, optionally with heating, or other methods. Heating is optional but preferred to facilitate the formation of the aqueous colloidal suspension of monophosphoryl lipid A. Suitable sonication equipment include, for example, a probe sonicator (Vibracell VCX600; Sonica) attached to probes whose sizes are appropriate for the volume being processed or a bath sonicator such as the Model No. G112SP1T obtained from Laboratory Supplies Co. Inc., (Hicksville, N.Y.). Other similar equipment used in the pharmaceutical industry would also be appropriate for sonication of monophosphoryl lipid A.

The aqueous colloidal suspension of monophosphoryl lipid A may be formed by methods other than sonication, for example, by shearing forces as would be generated in a microfluidizer.

Sugar is also added either before or after formation of the aqueous colloidal suspension, in amounts from 10 to 200 mg sugar per ml of aqueous diluent, preferably from about 20 to 150 mg/ml. The aqueous colloidal suspension, containing monophosphoryl lipid A, sugar and optionally an added amine based surfactant and optionally an immunologically effective amount of an antigen or antigens in the amounts recited hereinabove, is lyophilized to afford the lyophilized composition according to the present invention.

The aqueous colloidal suspension of monophosphoryl lipid A, sugar and, optionally, an amine based surfactant of an antigen or antigens is lyophilized to afford the lyophilized composition of the present invention. As is known to those skilled in the art, lyophilization is a process of drying in which water is sublimed from the product after it is frozen, by applying a vacuum. Specifics of lyophilizing or freeze-drying are described in Remington's Pharmaceutical Sciences. Chapter 84, page 1565, 18th Edition, A. R. Gennaro, Editor, 1990, Mack Publishing Company.

Whether an aqueous colloidal suspension is formed is determined by measuring the light transmission. It has been found that compositions having a light transmission of at least 88% exhibit the properties of colloidal suspensions. Light transmission is measured using a spectrophotometer in which is illuminated a liquid sample in a glass, quartz or plastic cuvette with a light path of 1 centimeter. The light may be in the visible or invisible spectrum, but for measurements of light transmission of this type a wavelength of 650 nm may appropriately be used. The amount of light passing through the sample (i.e. transmitted) is referenced to a blank cuvette containing the solvent or diluent in which the material is dissolved or suspended. Samples that do not absorb or scatter the light will exhibit 100% light transmission whereas those that absorb or scatter all the light will have 0% light transmission.

While not wishing to be bound by theory, it is believed that the advantageous results of the invention are obtained because the addition of sugar either before or after the formation of an aqueous colloidal suspension containing monophosphoryl lipid A prevents the monophosphoryl lipid A from aggregation either upon freezing or thawing of the aqueous colloidal suspension or upon lyophilizing the aqueous colloidal suspension and reconstitution or rehydration with an aqueous diluent. By including sugar in an aqueous colloidal suspension containing monophosphoryl lipid A prior to lyophilization, the lyophilized composition can be reconstituted with an aqueous diluent such as water or saline without the problem of reaggregation of the monophosphoryl lipid A. In addition, freezing of the reconstituted colloidal suspension or vaccine composition does not cause aggregation to reoccur. Similarly, by including sugar in an aqueous colloidal suspension containing monophosphoryl lipid A prior to freezing, upon thawing a frozen aqueous colloidal suspension is again obtained without the need for further sonication. The ability of sugar to prevent aggregation of the monophosphoryl lipid A is evident regardless of whether the aqueous colloidal suspension containing monophosphoryl lipid A is prepared in water alone, or in water containing triethylamine or triethanolamine.

Thus, the addition of sugar to monophosphoryl lipid A containing aqueous compositions, either before or after forming an aqueous colloidal suspension, provides surprising and unexpected results when such aqueous colloidal suspensions are either frozen and thawed or lyophilized and reconstituted. Such results further permit the advantageous preparation of vaccine compositions.

The following examples are provided to illustrate the invention.

EXAMPLE 1

Preparation of Turbid Mixture and Measurement of Light Transmission

Monophosphoryl lipid A (RIBI ImmunoChem., Hamilton, Mont.) is suspended in water at 1 mg/ml (w/v) forming a turbid mixture with visible white particulates of heterogeneous size. The turbid mixture is placed in a Shimadzu UV-1601, UV-Visible Spectrophotometer and illuminated with light of 650 nm wavelength. The turbid mixture allows 3.3% of the incident light to pass (i.e. transmission=3.3). An aqueous colloidal suspension is not found.

EXAMPLE 2

Preparation of Aqueous Colloidal Suspension and Measurement of Light Transmission Monophosphoryl lipid A, at 1 mg/ml (w/v) is suspended in water containing 0.5% triethanolamine (v/v) (5.62 mg/mL (w/v)) or 0.2% triethylamine (v/v) (1.46 mg/mL(w/v)). The samples are heated at 56–65° C. for 10–15 minutes and sonicated using either a probe sonicator (Vibracell VCX600) set at 30% power using a tapered microtip or a bath sonicator (Model No. G112SP1T, Laboratory Supplies Co. Inc., Hicksville, N.Y.) used at full power for 2 to 3 minutes. A clear suspension is obtained and placed in a Shimadzu UV-1601, UV-Visible Spectrophotometer and illuminated with light of 650 nm wavelength. The % light transmission is measured at $\geq 88\%$, indicating the formation of an aqueous colloidal suspension.

EXAMPLE 3

Preparation of Aqueous Colloidal Suspension of Monophosphoryl lipid A and Lyophilization Aqueous colloidal suspensions of monophosphoryl lipid A are formed by suspending monophosphoryl lipid A, at 1, 2 or 5 mg/mL (w/v) in water or water containing either 0.5% triethanolamine v/v (5.6 mg/mL w/v), or 0.2% triethylamine v/v (1.46 mg/mL w/v). Each Monophosphoryl lipid A suspension is heated for 10–15 minutes at 56° C. to 65° C. and then sonicated for a total of 2–3 minutes to obtain a clear suspension with no visual evidence of particulates. The samples (1 to 1.5 ml) are sonicated using either a probe sonicator (Vibracell VCX600) set at 30% power using a tapered microtip or a bath sonicator (Model No. G112SP1T, Laboratory Supplies Co. Inc., Hicksville, N.Y.) used at full power. Aliquots of the monophosphoryl lipid A aqueous colloidal suspensions above are diluted with an equal amount of water, or sucrose or dextrose solutions of varying concentrations. The resulting aqueous colloidal suspensions include monophosphoryl lipid A at 0.5, 1.0 or 2.5 mg/mL (w/v) and sucrose at final concentrations of 10, 50, 100 or 200 mg/ml (w/v) or dextrose at 10, 50, 100 or 170 mg/ml (w/v) as expressed in Table 1. The preparations contained either triethanolamine (TEM) at 2.81 or 5.62 mg/mL or triethylamine (TEA) at 0.73 mg/mL or no amine based surfactant. The samples are placed in a Shimadzu UV-1601, UV-Visible Spectrophotometer and illuminated with light of 650 nm wavelength. The % light transmission, as set forth in Table 1, ranges from 90.0 to 99.9%, indicating the formation of an aqueous colloidal suspension.

TABLE 1

COMPOSITION OF MONOPHOSPHORYL LIPID A FORMULATIONS

| Sample | MPL mg/mL | sugar added | sugar mg/mL | Amine added | Added Amine mg/mL | % light transmission |
|---|---|---|---|---|---|---|
| 1 | 0.5 | sucrose | 10 | TEM | 2.81 | 97.2 |
| 2 | 0.5 | dextrose | 10 | TEM | 2.81 | 97.1 |
| 3 | 0.5 | sucrose | 10 | TEM | 2.81 | 97.2 |
| 4 | 0.5 | dextrose | 10 | TEM | 2.81 | 97.3 |
| 5 | 0.5 | sucrose | 10 | TEA | 0.73 | 98.9 |
| 6 | 0.5 | sucrose | 10 | TEA | 0.73 | 98.4 |
| 7 | 0.5 | sucrose | 50 | TEM | 5.62 | 95.9 |
| 8 | 0.5 | sucrose | 50 | TEM | 5.62 | 96.0 |
| 9 | 0.5 | sucrose | 50 | TEM | 2.81 | 97.5 |
| 10 | 0.5 | dextrose | 50 | TEM | 2.81 | 97.4 |
| 11 | 0.5 | sucrose | 50 | TEM | 2.81 | 97.5 |
| 12 | 0.5 | dextrose | 50 | TEM | 2.81 | 97.4 |
| 13 | 0.5 | sucrose | 50 | TEA | 0.73 | 98.8 |
| 14 | 0.5 | sucrose | 50 | TEA | 0.73 | 99 |
| 15 | 0.5 | sucrose | 50 | — | 0 | 96.1 |
| 16 | 0.5 | sucrose | 50 | — | 0 | 96.0 |
| 17 | 0.5 | sucrose | 100 | TEM | 2.81 | 97.6 |
| 18 | 0.5 | dextrose | 100 | TEM | 2.81 | 97.6 |
| 19 | 0.5 | sucrose | 100 | TEM | 2.81 | 97.4 |
| 20 | 0.5 | dextrose | 100 | TEM | 2.81 | 97.6 |
| 21 | 0.5 | dextrose | 170 | TEM | 2.81 | 98.2 |
| 22 | 0.5 | dextrose | 170 | TEM | 2.81 | 98.1 |
| 23 | 0.5 | dextrose | 200 | TEM | 2.81 | 98.4 |
| 24 | 0.5 | sucrose | 200 | TEM | 2.81 | 98.4 |
| 25 | 0.5 | sucrose | 200 | TEM | 2.81 | 97.7 |
| 26 | 0.5 | sucrose | 200 | TEM | 2.81 | 97.8 |
| 27 | 0.5 | sucrose | 200 | TEA | 0.73 | 99.4 |
| 28 | 0.5 | sucrose | 200 | TEA | 0.73 | 99.4 |
| 29 | 0.5 | sucrose | 200 | TEA | 0.73 | 98.9 |
| 30 | 0.5 | sucrose | 200 | TEA | 0.73 | 98.9 |
| 31 | 1.0 | sucrose | 200 | TEA | 0.73 | 97.7 |
| 32 | 1.0 | sucrose | 200 | TEA | 0.73 | 97.6 |
| 33 | 1.0 | sucrose | 200 | TEM | 2.81 | 95.7 |
| 34 | 1.0 | sucrose | 200 | TEM | 2.81 | 95.6 |
| 35 | 2.5 | sucrose | 200 | TEM | 2.81 | 90.1 |
| 36 | 2.5 | sucrose | 200 | TEM | 2.81 | 90.0 |
| 37 | 2.5 | sucrose | 200 | TEA | 0.73 | 95.4 |
| 38 | 2.5 | sucrose | 200 | TEA | 0.73 | 95.3 |

Lyophilization of Monophosphoryl Lipid A Adjuvant Compositions

The aqueous colloidal suspensions set forth in Table 1 are lyophilized by first freezing the samples in glass vials or polypropylene culture tubes on dry ice pellets for at least 30 minutes. They are then transferred to large freeze drying vessels (Labconco) and connected to a Virtus Freeze Dryer. The samples are lyophilized for 18 hours at a vacuum of 250 millitors and the condenser temperature of −50° C. The composition of the lyophilized adjuvant compositions are shown in Table 2.

Reconstitution of Lyophilized Adjuvant Compositions

The lyophilized samples as set forth in Table 2 are reconstituted with either water or normal saline (0.9% NaCl w/v), the volume of which was equal to the volume of the aqueous colloidal suspension prior to lyophilization. Data showing the % light transmission of the samples after reconstitution with aqueous diluent are presented in Table 2. As shown in Table 2, the lyophilized compositions, containing sucrose or dextrose ranging from greater than 75% up to 99.4% of the composition by weight, gave rise to aqueous colloidal suspensions when rehydrated with water or saline. For samples 1–38 set forth in Table 2, the % transmission after rehydration ranged from 88.0% to 98.4% indicating the formation of an aqueous colloidal suspension. Samples 15 and 16, which contained 99% sugar by weight after lyophilization, were prepared without the addition of amines (triethylamine or triethanolamine) at the time of sonication. When rehydrated with either water or normal saline, % transmission values are measured at 96.1 and 93.6, respectively, indicating the formation of an aqueous colloidal suspension. These data show that when an aqueous colloidal suspension of Monophosphoryl lipid A prepared by sonication is lyophilized with an effective amount of sugar such as sucrose or dextrose it can be rehydrated with water or normal saline to regain an aqueous colloidal suspension.

TABLE 2

Light transmission properties of lyophilized Monophosphoryl Lipid A compositions after rehydration with water or normal saline.

| | Composition Wt. % after lyophilization | | | | % light transmission after rehydration |
|---|---|---|---|---|---|
| Sample | % MPL | % sugar | % Added Amine | Diluent for rehydration | |
| 1 | 3.8 | 75.1 | 21.1 | water | 95.8 |
| 2 | 3.8 | 75.1 | 21.1 | water | 96.1 |
| 3 | 3.8 | 75.1 | 21.1 | saline | 95.5 |
| 4 | 3.8 | 75.1 | 21.1 | saline | 95.4 |
| 5 | 4.5 | 89.0 | 6.5 | water | 96.5 |
| 6 | 4.5 | 89.0 | 6.5 | saline | 94.8 |
| 7 | 0.9 | 89.1 | 10 | water | 95.7 |
| 8 | 0.9 | 89.1 | 10 | saline | 95.7 |
| 9 | 0.9 | 93.8 | 5.3 | water | 96.0 |
| 10 | 0.9 | 93.8 | 5.3 | water | 96.6 |
| 11 | 0.9 | 93.8 | 5.3 | saline | 95.7 |
| 12 | 0.9 | 93.8 | 5.3 | saline | 96.3 |
| 13 | 1.0 | 97.6 | 1.4 | water | 98.4 |
| 14 | 1.0 | 97.6 | 1.4 | saline | 96.3 |
| 15 | 1.0 | 99.0 | 0 | water | 96.1 |
| 16 | 1.0 | 99.0 | 0 | saline | 93.6 |
| 17 | 0.5 | 96.8 | 2.7 | water | 96.4 |
| 18 | 0.5 | 96.8 | 2.7 | water | 97.1 |
| 19 | 0.5 | 96.8 | 2.7 | saline | 95.8 |
| 20 | 0.5 | 96.8 | 2.7 | saline | 96.8 |
| 21 | 0.3 | 98.1 | 1.6 | water | 97.4 |
| 22 | 0.3 | 98.1 | 1.6 | saline | 96.6 |
| 23 | 0.2 | 98.4 | 1.4 | water | 97.7 |
| 24 | 0.2 | 98.4 | 1.4 | saline | 96.8 |
| 25 | 0.2 | 98.4 | 1.4 | water | 97.2 |
| 26 | 0.2 | 98.4 | 1.4 | saline | 96.9 |
| 27 | 0.2 | 99.4 | 0.4 | water | 98.4 |
| 28 | 0.2 | 99.4 | 0.4 | saline | 96.7 |
| 29 | 0.2 | 99.4 | 0.4 | water | 95.5 |
| 30 | 0.2 | 99.4 | 0.4 | saline | 96.7 |
| 31 | 0.5 | 99.1 | 0.4 | water | 97.1 |
| 32 | 0.5 | 99.1 | 0.4 | saline | 96.1 |
| 33 | 0.5 | 98.1 | 1.4 | water | 95.0 |
| 34 | 0.5 | 98.1 | 1.4 | saline | 94.6 |
| 35 | 1.2 | 97.4 | 1.4 | water | 89.8 |
| 36 | 1.2 | 97.4 | 1.4 | saline | 88.0 |
| 37 | 1.2 | 98.4 | 0.4 | water | 94.8 |
| 38 | 1.2 | 98.4 | 0.4 | saline | 90.8 |

EXAMPLE 4

Using the procedures set forth in Example 3, formulations containing monophosphoryl lipid A, sugar and amine in the amounts set forth in Table 3 are prepared. The light transmission of these formulations is measured and as set forth in Table 3, % light transmission ranges from 95.4 to 98.8% indicating the formation of an aqueous colloidal suspension.

TABLE 3

COMPOSITION OF MONOPHOSPHORYL LIPID A FORMULATIONS

| Sample | MPL mg/mL | sugar added | sugar mg/mL | Amine added | Added Amine mg/mL | % Light Transmission |
|---|---|---|---|---|---|---|
| 39 | 0.5 | — | 0 | TEM | 5.62 | 95.8 |
| 40 | 0.5 | — | 0 | TEM | 2.81 | 97.1 |
| 41 | 0.5 | — | 0 | TEA | 0.73 | 98.8 |
| 42 | 0.5 | — | 0 | — | 0 | 95.8 |
| 43 | 0.5 | — | 0 | — | 0 | 95.9 |
| 44 | 0.5 | sucrose | 0.5 | TEM | 5.62 | 95.5 |
| 45 | 0.5 | sucrose | 1 | TEM | 5.62 | 95.4 |
| 46 | 0.5 | sucrose | 5 | TEM | 5.62 | 95.5 |
| 47 | 0.5 | sucrose | 10 | TEM | 5.62 | 95.6 |

Using the procedures set forth in Example 3, the formulations of Table 3 are lyophilized and reconstituted with water or saline as set forth in Table 4.

TABLE 4

Light transmission properties of lyophilized Monophosphoryl Lipid A formulations after rehydration with water or normal saline.

| Sample | Wt. % of Composition after lyophilization | | | Diluent for rehydration | % light transmission after rehydration |
|---|---|---|---|---|---|
| | % MPL | % sugar | % Added Amine | | |
| 39 | 8.2 | 0.0 | 91.8 | water | 58.6 |
| 40 | 15.1 | 0.0 | 84.9 | water | 58.2 |
| 41 | 40.7 | 0.0 | 59.3 | water | 22 |
| 42 | 100.0 | 0.0 | 0 | water | 32.8 |
| 43 | 100.0 | 0.0 | 0 | saline | 30.2 |
| 44 | 7.6 | 7.6 | 84.9 | water | 63.1 |
| 45 | 7.0 | 14.0 | 78.9 | water | 64.7 |
| 46 | 4.5 | 45.0 | 50.5 | water | 50.6 |
| 47 | 3.1 | 62.0 | 34.9 | water | 83.5 |

When samples lyophilized without sugars (samples 39–43) are rehydrated with water or saline the resultant preparation is turbid with suspended particulates. These samples exhibit a % transmission ranging from 22.0 to 58.6. Similar results are obtained when samples 44–47 containing 7.6% to 62.0% sugar are rehydrated with water indicating that an aqueous colloidal suspension is not formed.

EXAMPLE 5

Freezing and Thawing of Monophosphoryl Lipid A Sonicated in Aqueous Triethylamine in the Presence of Sucrose Monophosphoryl lipid A is sonicated in water containing 0.2% triethylamine (v/v) and then admixed with an equal volume of water or with water containing added sucrose to yield a clear suspension containing monophosphoryl lipid A at 0.5 mg/mL (w/v) without sucrose or containing 100 mg/mL sucrose w/v and triethylamine at a final concentration of 0.1% v/v (0.73 mg/mL w/v). The samples (48 and 49) are placed in a Shimadzu UV-1601, UV-Visible Spectrophotometer and illuminated with light of 650 nm and each allowed 98.8% of the light to pass thus indicating the formation of an aqueous colloidal suspension. The colloidal suspensions are frozen and then thawed. Upon thawing, the monophosphoryl lipid A preparation without sucrose (sample 48) is turbid with particulates and has a % light transmission of 60.3% as measured in a Shimadzu UV-1601, UV-Visible Spectrophotometer and illuminated with light of 650 nm wavelength indicating that an aqueous colloidal suspension is not formed. The monophosphoryl lipid A containing sucrose (sample 49) remains clear after freezing and thawing and has a % light transmission of 97.8% as measured in a Shimadzu UV-1601, UV-Visible Spectrophotometer and illuminated with light of 650 nm wavelength indicating the formation of an aqueous colloidal suspension. These data are displayed in Table 5.

TABLE 5

Light transmission properties before and after freezing and. thawing of Monophosphoryl Lipid A sonicated with triethylamine and diluted with or without sucrose

| Sample | Composition of MPL preparations | | | % light transmission | | Appearance after thawing |
|---|---|---|---|---|---|---|
| | MPL (mg/mL) | Sucrose (mg/mL) | Added TEA (mg/mL) | Before freezing | After thawing | |
| 48 | 0.5 | 0 | 0.73 | 98.8 | 60.3 | Turbid |
| 49 | 0.5 | 100 | 0.73 | 98.8 | 97.3 | Clear |

EXAMPLE 6

Preparation of Vaccine Compositions a. Preparation of Aqueous Colloidal Suspensions of Monophosphoryl Lipid A Using the procedures set forth in Example 3 above, a mixture of monophosphoryl lipid A in water of about 0.5 mg/ml and an amine-based surfactant triethanolamine at about 2.8 mg/ml is heated and sonicated to give an aqueous colloidal suspension. Either before or after sonication, but prior to freezing or lyophilizing, sucrose is added at a final concentration between about 10 to 200 mg/ml. The aqueous colloidal suspension so obtained may be either frozen and thawed for use in a vaccine composition or lyophilized and reconstituted with an aqueous diluent for use in a vaccine composition.

b. Preparation of an Aqueous Vaccine Composition From Frozen Monophosphoryl Lipid A Composition The aqueous colloidal suspension of monophosphoryl lipid A, sucrose and triethanolamine prepared as in (a) above is frozen. It is then thawed and combined with an aqueous diluent containing an antigen, for example, a pneumococcal glycocon-jugate prepared according to U.S. Pat. No. 5,360,897, to obtain a vaccine composition containing up to about 400 micrograms monophosphoryl lipid A per ml and up to about 200 micrograms pneumococcal glycoconjugate per ml. To obtain a vaccine composition containing 400 micrograms of monophosphoryl lipid A and 200 micrograms of pneumococcal glycoconjugate, for example, 0.8 ml of the thawed colloidal suspension may be combined with 200 micrograms of pneumococcal glycocongugate in 0.2 ml of water. This vaccine composition may then be administered to a vertebrate, preferably to a human, using about 0.1 to 1.0 ml per dose.

c. Preparation of an Aqueous Vaccine Composition from Lyophilized Monophosphoryl Lipid A Composition The aqueous colloidal suspension of monophosphoryl lipid A, sucrose and triethanolamine prepared in (a) above is lyophilized. It is then reconstituted with an aqueous diluent containing an antigen, for example, a pneumococcal glycoconjugate prepared according to U.S. Pat. No. 5,360,897, to obtain a vaccine composition containing up to about 400 micrograms monophosphoryl lipid A per ml and up to about 200 micrograms pneumococcal glycoconjugate per ml. This vaccine composition may then be administered to a vertebrate, preferably to a human, using about 0.1 to 1.0 ml per dose.

d. Preparation of a Frozen Aqueous Vaccine Composition

To the aqueous colloidal suspension of monophosphoryl lipid A, sucrose and triethanolamine prepared in (a) above is added an antigen, for example, a pneumococcal glycoconjugate prepared according to U.S. Pat. No. 5,360,897 to obtain a vaccine composition. The vaccine composition is then frozen. The concentrations of monophosphoryl lipid A and pneumococcal glycoconjugate are adjusted by addition of a aqueous diluent, to up to about 400 micrograms per ml and up to about 200 micrograms per ml, respectively, either before freezing or after freezing and thawing, provided that the sucrose is kept at a concentration of about 10 to 200 mg/ml before freezing. The frozen and thawed vaccine composition may then be administered to a vertebrate, preferably to a human, using about 0.1 to 1.0 ml per dose.

e. Preparation of a Lyophilized Vaccine Composition

To the aqueous colloidal suspension of monophosphoryl lipid A, sucrose and triethanolamine prepared in (a) above is added, for example, a pneumococcal glycoconjugate prepared according to U.S. Pat. No. 5,360,897 to obtain a vaccine composition. The antigen may be added either before or after the heating and sonicating steps. The amount of pneumococcal glycoconjugate added is calculated such that, upon subsequent reconstitution of the lyophilized vaccine composition, the aqueous mixture will contain up to about 400 micrograms of monophosphoryl lipid A per ml and up to about 200 micrograms pneumococcal glycoconjugate per ml. The vaccine composition is then lyophilized. Following lyophilization, the composition is reconstituted with an aqueous diluent. This reconstituted aqueous vaccine composition may then be administered to a vertebrate, preferably to a human, using about 0.1 to 1.0 ml per dose.

What is claimed:

1. A method for the preparation of an aqueous colloidal suspension containing 3-O-desacyl-4'-monophosphoryl lipid A capable of being frozen and thawed comprising:
   a. suspending 3-O-desacyl-4'-monophosphoryl lipid A in an amount from 0.5 mg/ml up to 5 mg/ml and, an amine based surfactant in an amount from 0 to about 6 mg/ml in an aqueous diluent;
   b. forming an aqueous colloidal suspension having a light transmission of greater than or equal to 88%, as measured spectrophotometrically;
   c. adding sugar at about 10 to 200 mg/ml either before or after forming the aqueous colloidal suspension;
   d. freezing the sugar containing aqueous colloidal suspension; and
   e. thawing and recovering the aqueous colloidal suspension without sonication to prepare an aqueous colloidal suspension.

2. The method of claim 1, wherein said thawed aqueous colloidal suspension is combined with an aqueous diluent further containing an antigen or antigens, additional adjuvant or a pharmaceutically acceptable preservative, carrier or vehicle.

3. The method of claim 2 wherein said additional adjuvant is aluminum phosphate.

4. The method according to claim 2 wherein the antigen or antigens are from or produced by a bacterium, a virus, a parasite, a cancer cell or an allergen.

5. The method according to claim 4 wherein the antigen is a Chlamydia, Nontypeable *Haemophilus influenzae, Helicobacter pylon, Moraxella catarrhalis, Neisseria gonorrhoeae, Neisseria meningitidis, Salmonella typhi, Streptococcus pneumoniae*, Group A Streptococci, Group B Streptococcus, Herpes Simplex Virus, Human Immunodeficiency Virus, Human Papilloma Virus, Influenza Virus, Measles, Parainfluenza, Respiratory Syncytial Virus, Rotavirus, or Norwalk Virus antigen.

6. The method according to claim 5 wherein the antigen is a conjugate comprising capsular polysaccharide of *Streptococcus pneumoniae* covalently attached to a protein.

7. The method according to claim 1 the sugar comprises dextrose, mannose, galactose, fructose, sucrose, lactose, isomaltose, maltose or trehalose.

8. The method according to claim 7 wherein the sugar is sucrose or dextrose.

9. The method according to claim 1 wherein the amine based surfactant is triethylamine or triethanolamine.

10. A method for the preparation of an aqueous colloidal suspension containing 3-O-desacyl-4'-monophosphoryl lipid A capable of being lyophilized and resuspended comprising:
    a. suspending 3-O-desacyl-4'-monophosphoryl lipid A in an amount from 0.5 mg/ml up to 5 mg/ml and, an amine based surfactant in an amount from 0 to about 6 mg/ml in an aqueous diluent;
    b. forming an aqueous colloidal suspension having a light transmission of greater than or equal to 88%, as measured spectrophotometrically;
    c. adding sugar at about 10 to 200 mg/ml either before or after forming the aqueous colloidal suspension;
    d. lyophilizing the sugar containing aqueous colloidal suspension to obtain a lyophilized composition;
    e. reconstituting the lyophilized composition without sonication with an aqueous diluent at an amount from 10 to 210 mg of the lyophilized composition per ml of aqueous diluent, and
    f. obtaining an aqueous composition in the form of an aqueous colloidal suspension having a light transmission of greater than or equal to 88% as measured spectrophotometrically without sonication.

11. The method of claim 10 wherein said aqueous colloidal suspension is combined with an aqueous diluent further containing an antigen or antigens, additional adjuvant or a pharmaceutically acceptable preservative, carrier or vehicle.

12. The method of claim 11 wherein said additional adjuvant is aluminum phosphate.

13. The method according to claim 11 wherein the antigen or antigens are from or produced by a bacterium, a virus, a parasite, a cancer cell or an allergen.

14. The method according to claim 13 wherein the antigen is a Chlamydia, Nontypeable *Haemophilus influenzae, Helicobacter pylori, Moraxella catarrhalis, Neisseria gonorrhoeae, Neisseria meningitidis, Salmonella typhi, Streptococcus pneumoniae,* Group A Streptococci, Group B Streptococcus, Herpes Simplex Virus, Human Immunodeficiency Virus, Human Papilloma Virus, Influenza Virus, Measles, Parainfluenza, Respiratory Syncytial Virus, Rotavirus, or Norwalk Virus antigen.

15. The method according to claim 14 wherein the antigen is a conjugate comprising capsular polysaccharide of *Streptococcus pneumoniae* covalently attached to a protein.

16. The method according to claim 10 wherein the sugar comprises dextrose, mannose, galactose, fructose, sucrose, lactose, isomaltose, maltose or trehalose.

17. The method according to claim 16 wherein the sugar is sucrose or dextrose.

18. The method according to claim 10 therein the amine based surfactant is triethylamine or triethanolamine.

* * * * *